United States Patent [19]

Hahn

[11] Patent Number: 5,297,732
[45] Date of Patent: Mar. 29, 1994

[54] FRAGRANCE-EMITTING CONTAINER

[76] Inventor: Gary S. Hahn, 2371 Lagood View Dr., Cardiff by the Sea, Calif. 92007

[21] Appl. No.: 942,064

[22] Filed: Oct. 16, 1992

Related U.S. Application Data

[63] Continuation-in-part of Ser. No. 666,872, Mar. 8, 1991, Pat. No. 5,165,603.

[51] Int. Cl.⁵ .................................................. A61L 9/04
[52] U.S. Cl. ........................................ 239/55; 239/53; 239/34; 206/825; 220/506
[58] Field of Search ................... 239/53, 55, 56, 34, 239/36, 44, 47; 312/31, 31.01; 206/205, 210, 581, 823; 220/500, 505, 506

[56] References Cited

U.S. PATENT DOCUMENTS

| | | | |
|---|---|---|---|
| 2,131,975 | 10/1938 | Samstag | 239/55 |
| 2,481,095 | 9/1949 | Essman | 220/506 |
| 3,826,358 | 7/1974 | Butler et al. | 312/31 |
| 3,877,571 | 4/1975 | Sanford | 206/205 |
| 4,772,300 | 9/1988 | Cullen et al. | 312/31 |
| 5,004,106 | 4/1991 | Blumstock et al. | 206/823 |
| 5,025,817 | 6/1991 | Wen | 206/823 |
| 5,064,624 | 11/1991 | King | 239/34 |
| 5,165,603 | 11/1992 | Hahn | 220/506 |

FOREIGN PATENT DOCUMENTS

| | | | |
|---|---|---|---|
| 550062 | 12/1957 | Canada | 312/31 |
| 354909 | 12/1937 | Italy | 220/506 |
| 172535 | 10/1934 | Switzerland | 220/506 |
| 265453 | 2/1927 | United Kingdom | 312/31 |

*Primary Examiner*—Andres Kashnikow
*Assistant Examiner*—Christopher G. Trainor
*Attorney, Agent, or Firm*—Lyon & Lyon

[57] ABSTRACT

A fragrance-emitting container has a container body, a container lid and a fragrance reservoir well. A fragrance reservoir is positionable in the reservoir well. Screw threads, a sliding friction attachment or other means are used for securing the lid to the container body. A seal is provided between the body and lid to seal in the fragrance when the container is closed. The fragrance emitter is incorporated into the container so that the container contents can be kept substantially free of fragrance producing chemicals which may irritate the skin.

7 Claims, 10 Drawing Sheets

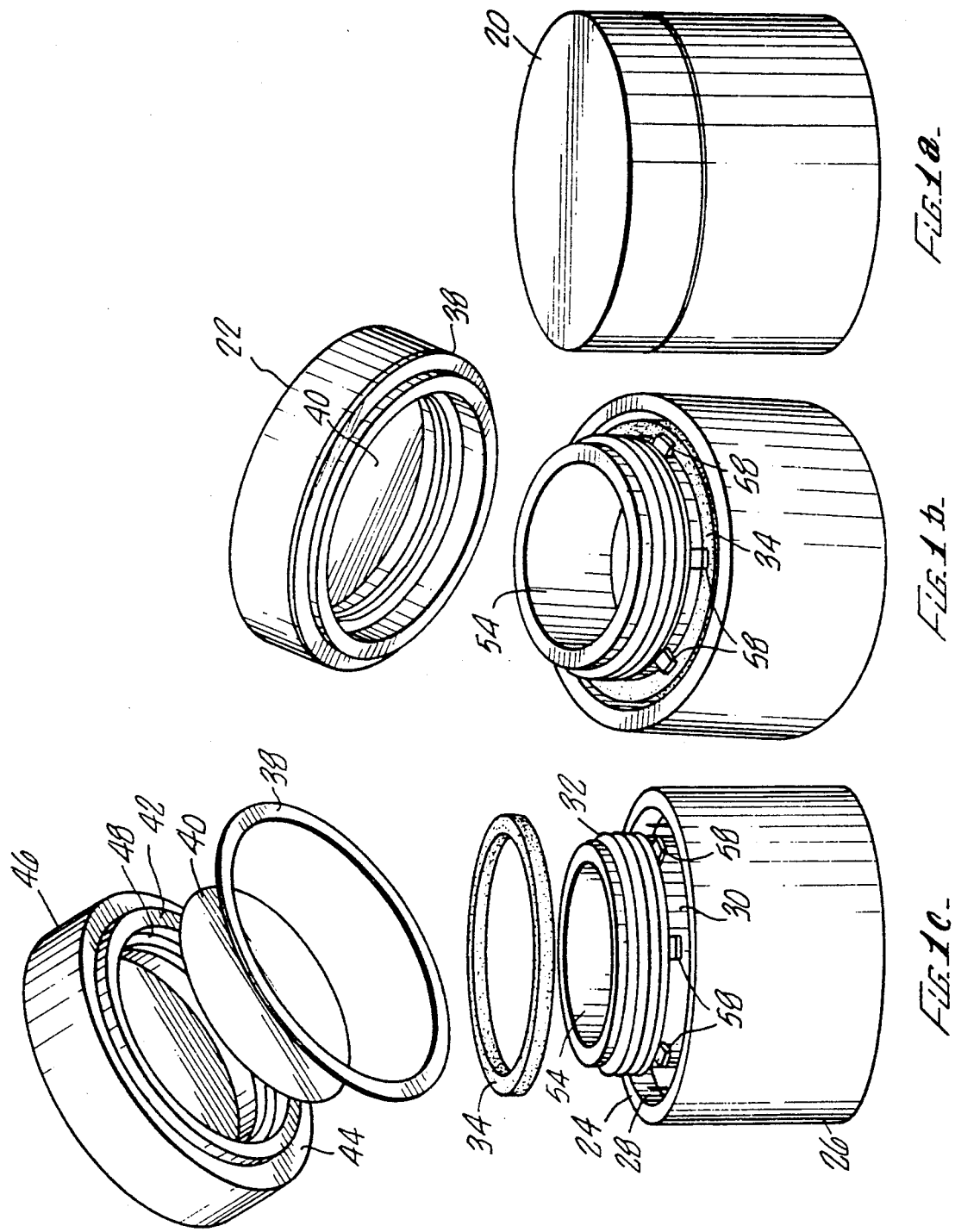

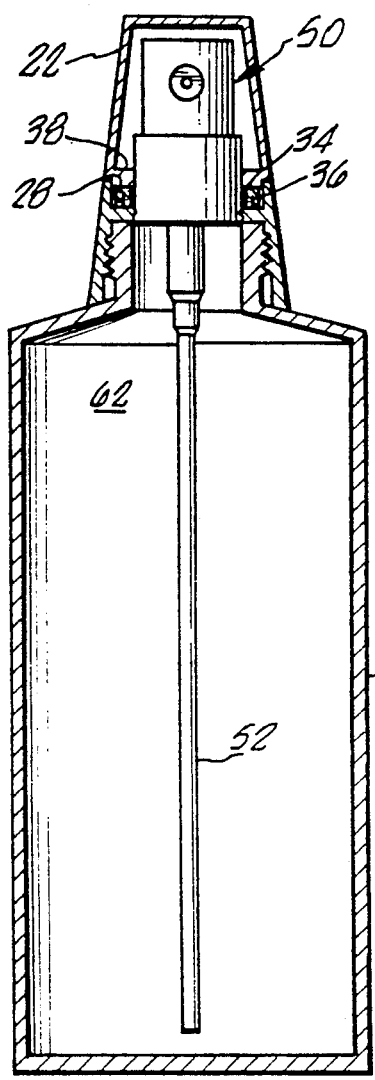
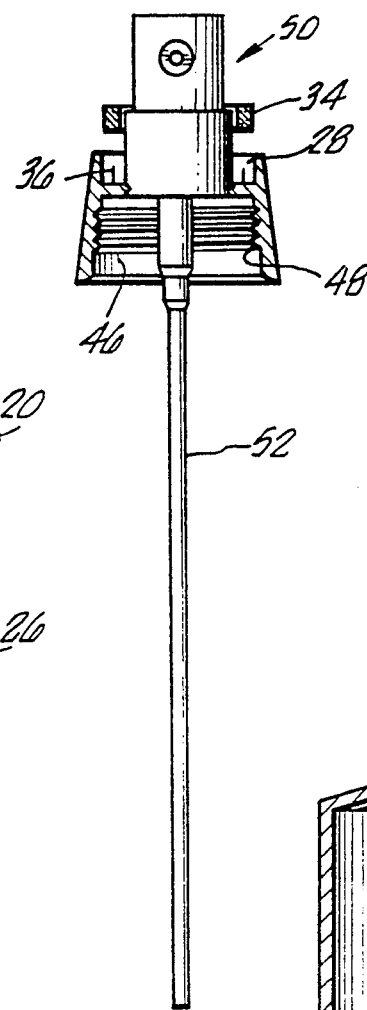
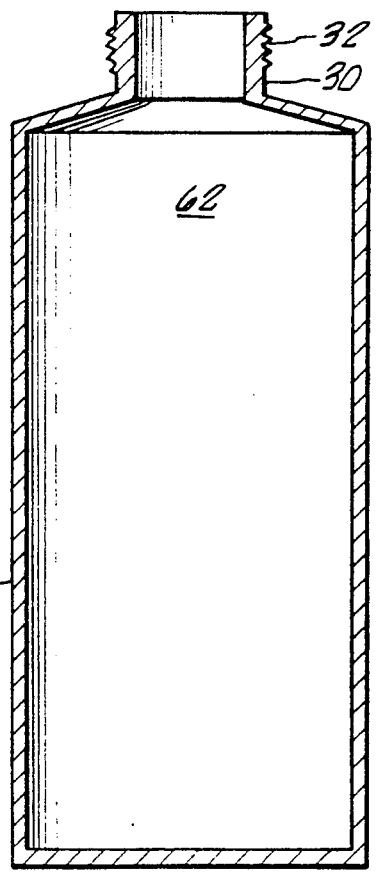
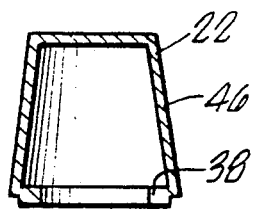

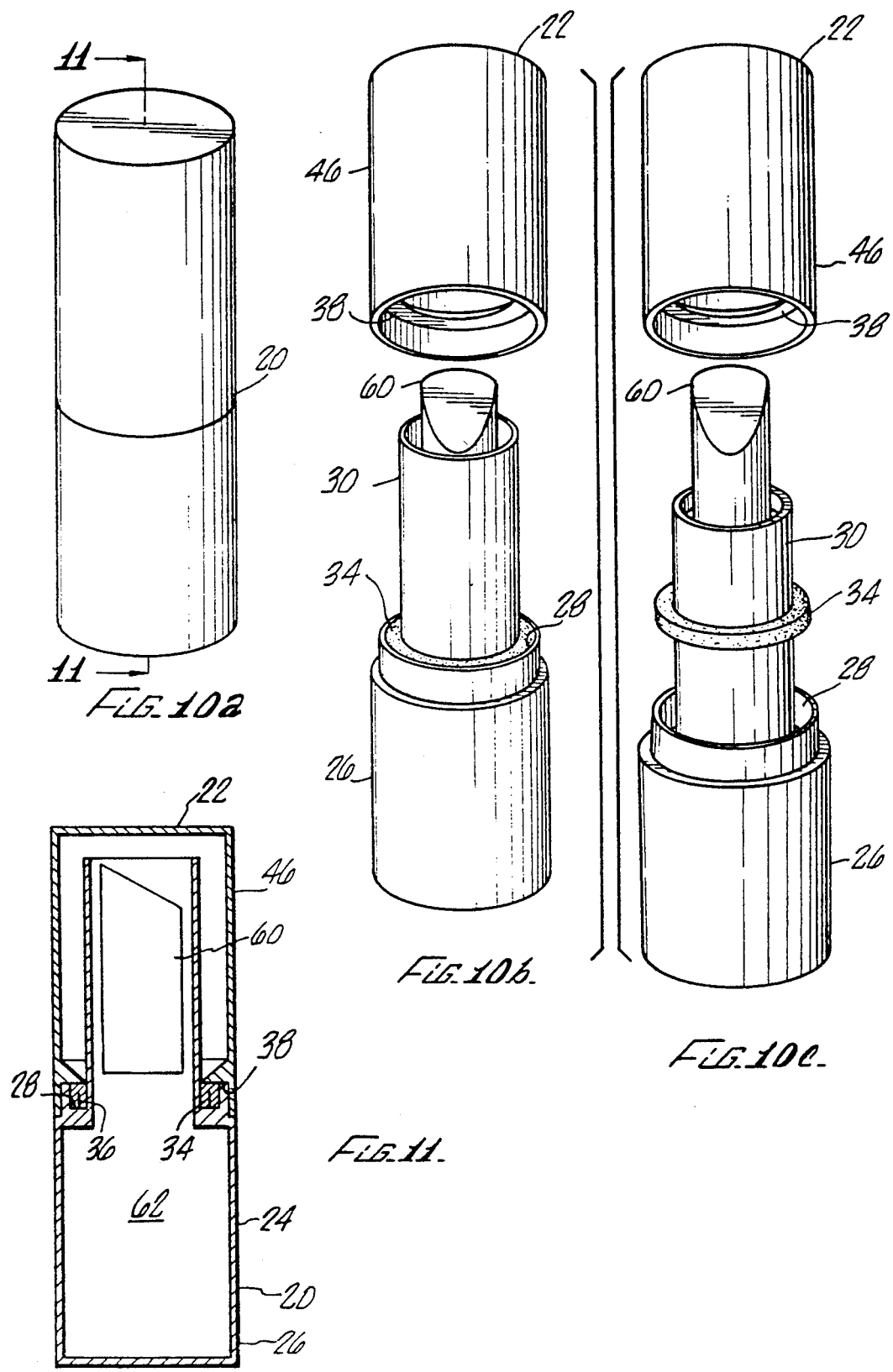

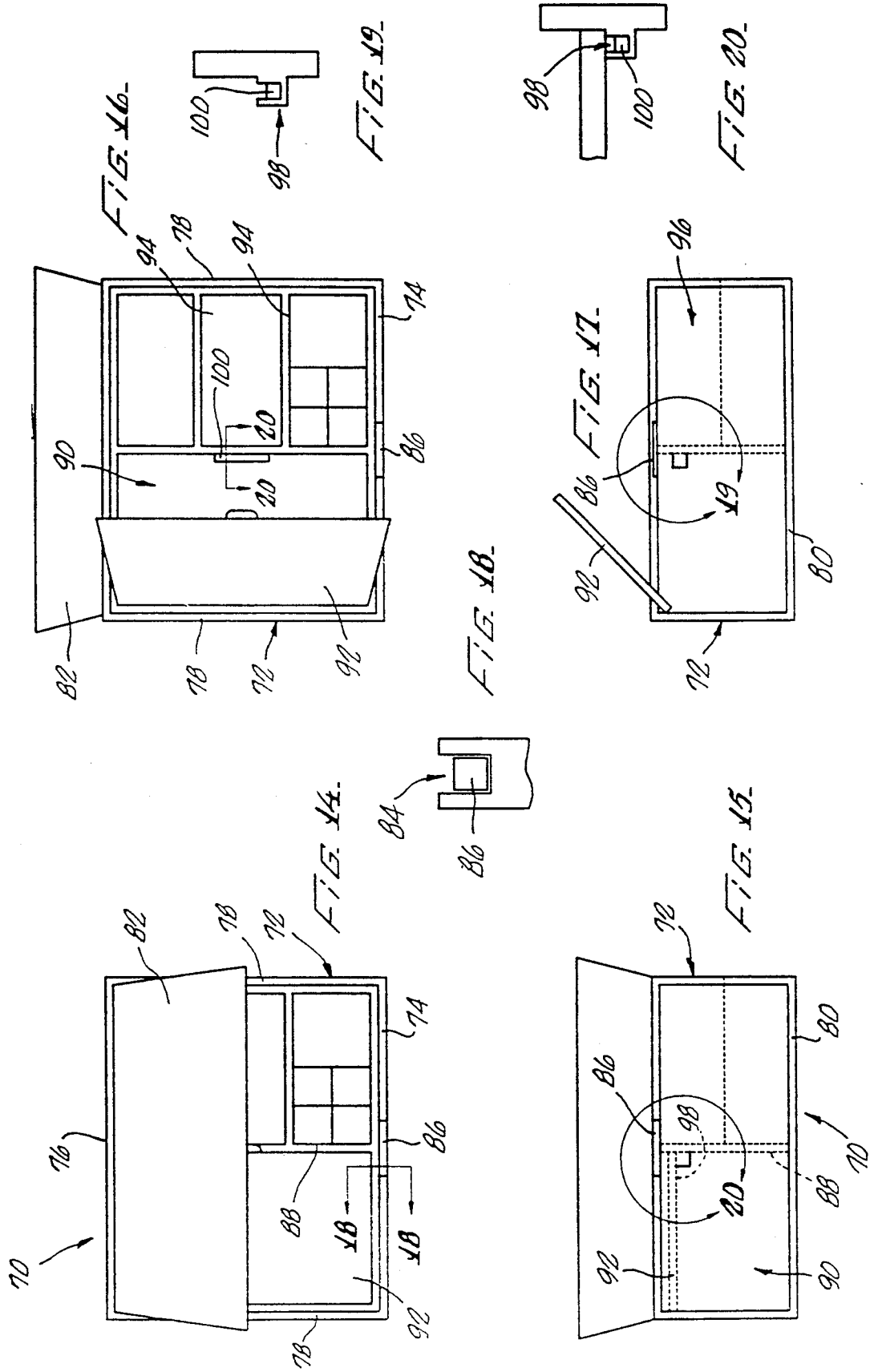

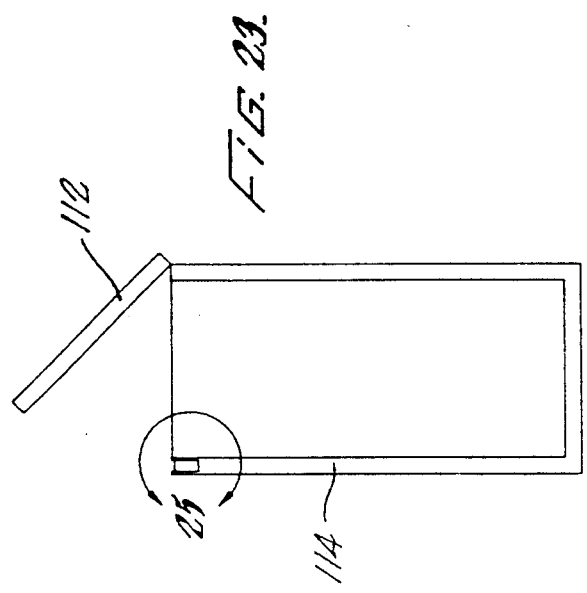
FIG. 23.
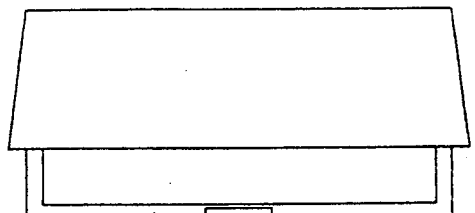
FIG. 24.
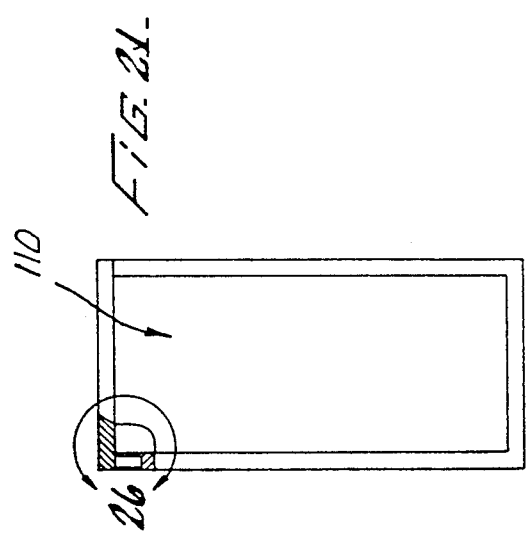
FIG. 21.
FIG. 22.
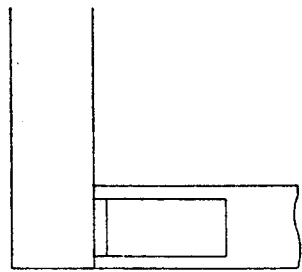
FIG. 26.
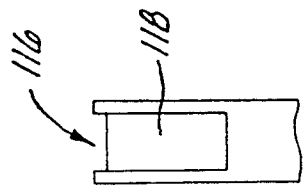
FIG. 25.

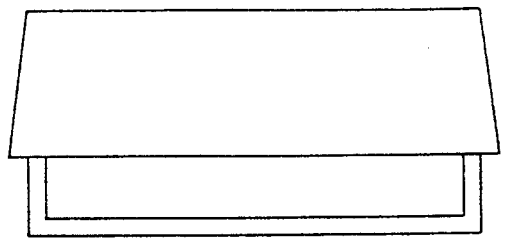
FIG. 30.
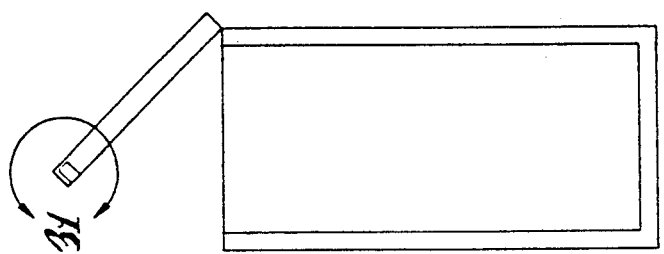
FIG. 29.
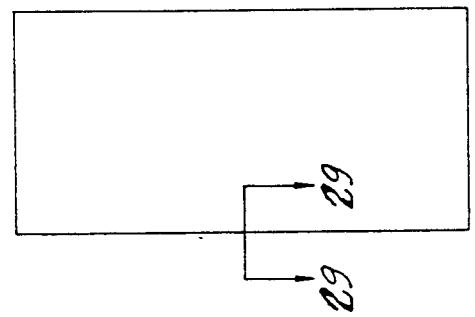
FIG. 28.
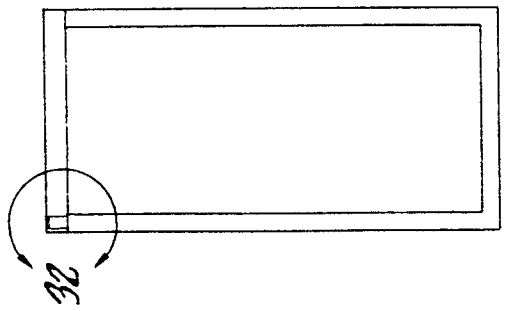
FIG. 27.
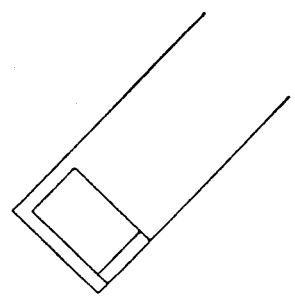
FIG. 31.
FIG. 32.

FRAGRANCE-EMITTING CONTAINER

This is a continuation-in-part of my U.S. patent application No. 07/666,872, filed Mar. 8, 1991 and now U.S. Pat. No. 5,165,603.

BACKGROUND OF THE INVENTION

Many substances are applied to the skin of humans or animals in order to alter the appearance of the skin or other tissue or body part, to protect the skin from the environment, or to produce a biological change in the skin for therapeutic purposes. These substances are generically termed "skin care products" and may be in the form of solids, liquids, suspensions, semisolids in the form of creams, gels or pastes, powders or finely dispersed liquids in the form of a spray or mist. In all cases, these products contain chemicals which may produce irritation or inflammation when applied to the skin.

The magnitude of skin care product-induced irritation may range from mild to severe and may be accompanied by subjective sensations which include stinging, burning, itching and tingling. Objective signs of irritation, if present, may include erythema (redness), edema (swelling), exudation (weeping), blistering or fissuring of the skin. The irritation response may be due to the direct effect of certain chemicals in skin products on the skin or to a response by the immune system directed toward the chemicals in combination with skin components (e.g., allergic contact dermatitis).

Whatever the exact cause of irritation, many attempts have been made to reduce the irritation potential of skin care products by identifying chemicals which tend to cause irritation and eliminating them from products. Many of these products are advertised to consumers as "hypoallergenic" to designate the product's reduced tendency to cause irritation in consumers with sensitive skin.

Among the many substances which frequently cause irritation, chemicals used for their perceived fragrance ("fragrances") have been found to be among the most frequent irritants. Based on these findings, products advertised as "hypoallergenic" or for "sensitive skin" are often labeled "fragrance-free" to represent their lack of potentially irritating fragrance chemicals.

It is well known that humans value pleasant-smelling fragrances as evidenced by their frequent use by both men and women. Consumers spend billions of dollars per year to purchase perfumes, colognes, air fresheners and other scented products which produce desirable fragrances. The fact that many skin care products continue to be sold which contain fragrances even though fragrance chemicals may produce irritation, attests to the value placed on fragrances.

Beyond the subjective enjoyment produced by pleasant fragrances, there may be additional value to sensing pleasant fragrances. For example, the concept of "aromatherapy" suggests that exposure to certain fragrances may produce beneficial psychological and physiological responses such as stress reduction due to activation of brain centers (e.g., the limbic system) which are especially responsive to fragrances.

Consumers with sensitive skin who must use hypoallergenic, fragrance-free skin care products do not derive the enjoyment and potential benefit of pleasant fragrances in skin care products.

The apparent strength or intensity of a fragrance is dependent on the length of time the fragrance is inhaled. This phenomenon is termed "odor adaptation" or "olfactory fatigue". Upon initial exposure to a fragrance, the perceived intensity is maximum. After several minutes of exposure, the perceived intensity is substantially reduced, due to diminished sensitivity of the fragrance-sensing olfactory receptor cells and higher brain olfactory centers. After several additional minutes, many people are not able to detect the fragrance on themselves, especially if it was applied in close proximity to the nose.

With the exception of perfumes, colognes and other products having the primary purpose of emitting a fragrance, most skin care products usually contain a relatively low amount of fragrance-producing chemicals which are intended to produce a "low intensity" fragrance. Upon application of such scented products, the consumer is likely to perceive the fragrance for only a short period of time, frequently only during the time period during which the product is applied to the skin. This observation suggests that most of the "fragrance benefit" obtained by a consumer using scented skin care products is of several minutes duration, after which the average consumer is usually not aware of the continuing presence of the fragrance on their skin. The fragrance-producing chemicals, by contrast, continue to interact with the skin until they are washed off during which time irritation may occur.

In addition to fragrances, humans and animals may enjoy and benefit from inhaling volatile substances which may not have a detectable scent, but which none-the-less produce a distinct biological or psychological effect. These substances include, but are not limited to pheromones which may alter the sexual behavior of humans or animals, hormones which may alter the physiology of the body, mood-altering substances, appetite-altering substances, organ extracts, plant extracts or other materials or chemicals which provide a desired biological or psychological effect.

In addition to fragrances which may benefit humans or animals directly, certain volatile chemicals may benefit humans or animals indirectly by their effect on insects, animals or other living organisms. For example, substances which repel insects or animals are very useful for many purposes. The use of the terms "fragrance" or "fragrance chemicals" herein includes all of the aforementioned substances as well.

The many beneficial effects or fragrances occur when relatively small quantities of their volatile chemical components are sensed by humans, animals or other living organisms. By contrast, direct physical contact or ingestion of the concentrated fragrance chemicals by a living organism may produce undesired and potentially toxic effects. Similarly, if fragrance chemicals physically contact inanimate objects, untoward or damaging effects may occur due the chemical reactivity of the fragrance chemicals.

It is well known, for example, that fragrances in skin care products can produce irritation and allergic reactions in many people. Similarly, insect repellents which are applied to the skin of humans or animals can produce systemic toxic reactions. Fragrance chemicals may also stain clothes or may chemically react with fabrics or other materials. In other applications, it may be impractical to expose the contents of a container to fragrances, for example, in waste containers.

It is also a object of the present invention to provide products and methods which will provide the benefits of the volatile components of fragrance chemicals while simultaneously eliminating the undesirable effects which may occur when the concentrated fragrance chemicals contact the body or inanimate objects.

It is an object of the present invention to provide containers and methods which will enable a consumer who uses fragrance-free skin care products to enjoy fragrances which are not mixed with the actual skin care product formulation. Thus, the consumer will be able to enjoy the pleasant fragrance associated with the application of a skin care product without risking the chance of fragrance-induced skin irritation.

It is also an object of the invention to provide a fragrance emitting container which can be used in applications where it is not desirable, practical or convenient to incorporate fragrance producing chemicals into the formulation of the contained product itself.

SUMMARY OF THE INVENTION

Hence, a consumer would achieve essentially the same benefit and pleasure from fragrance exposure if the fragrance were not mixed into the skin care product formulation, but was instead released by the container during the time when the product was being applied to the skin. Since most consumers are aware of a skin care product's fragrance for only several minutes, they will achieve a similar transient period of fragrance awareness if the fragrance is released by the container instead of by the skin care product formulation itself.

The present containers and methods release fragrances which are perceived during the time the container's contents are being used. The containers are designed to release one or more fragrances during and after the process of opening the container by the user.

The fragrance-producing chemicals are stored in a fragrance emitter or "fragrance reservoir" which is located in either the container itself, or in the container's lid or cap, or in a subassembly thereof. The reservoir may be constructed of many different materials, an essential attribute of which is a sufficient porosity or physical structure which allows the fragrance-producing chemicals to be released in adequate amounts over the intended useful life of the product. Especially preferred materials for the fragrance reservoir are porous, flexible or elastomeric polymers which are non-reactive with the fragrance-producing chemicals and which retain and release the fragrance chemicals into the air for an extended period of time.

An important aspect of the invention is that fragrance chemicals do not contact the contents of the container and thus cannot produce irritation or other undesirable effect on the user.

BRIEF DESCRIPTION OF THE DRAWINGS

In the drawings, wherein similar reference characters denote similar elements throughout the several views:

FIG. 1a is a perspective view of a fragrance-emitting container;

FIG. 1b is a perspective view of a container of FIG. 1a with the lid removed;

FIG. 1c is an exploded view of the container of FIG. 1a;

FIG. 2c is an exploded view of the container of FIG. 2a;

FIG. 3 is a section view taken along line 3—3 of FIG. 1a;

FIG. 4 is an exploded section view of the container of FIG. 1a;

FIG. 5c is a perspective view of the container body of the container of 5a;

FIG. 5d is an exploded perspective view of the spray mechanism, fragrance reservoir and lid of the container of FIG. 5a;

FIG. 6 is a section view taken along line 6—6 of FIG. 5a;

FIG. 7 is a front section elevation view of the pump mechanism of the container of FIG. 5a;

FIG. 8 is a section view of the lid thereof;

FIG. 9 is a section view of the container body thereof;

FIG. 10a is a perspective view of a fragrance-emitting lipstick container;

FIG. 10b is a perspective view thereof with lid removed;

FIG. 10c is a partially exploded perspective view thereof;

FIG. 11 is a section view taken along line 11—11 of FIG. 10a, with the lipstick advancing mechanism omitted for clarity of illustration.

FIG. 14 is a top view of another embodiment which may be a cosmetic organizer;

FIG. 15 is a side view thereof showing the main cover partially opened;

FIG. 16 is a top view thereof showing the main cover fully opened and an interior compartment cover partially opened;

FIG. 17 is a side view thereof;

FIG. 18 is an enlarged section view fragment taken along line 18—18 of FIG. 14;

FIG. 19 is an enlarged section view fragment taken along line 19—19 of FIG. 16;

FIG. 20 is a partial section view of the channel and reservoir shown in FIG. 19 with the interior compartment cover closed over the channel;

FIG. 21 is a side elevation view, in part section, of another embodiment which may be a trash container;

FIG. 22 is a top view thereof;

FIG. 23 is a section view taken along line 23—23 of FIG. 22;

FIG. 24 is a plan view of the container of FIG. 23;

FIG. 25 is an enlarged section view fragment of the channel and fragrance reservoir of FIG. 23;

FIG. 26 is a partial section view fragment of the channel and fragrance reservoir of FIG. 25 with the container cover closed and substantially sealing the fragrance reservoir;

FIG. 27 is a side elevation view, in part section, of another embodiment having a fragrance reservoir in a container lid or cover;

FIG. 28 is a top view thereof;

FIG. 29 is a partial section view taken along line 29—29 of FIG. 28;

FIG. 30 is a plan view of the container of FIG. 29;

FIG. 31 is an enlarged section view fragment of the lid and fragrance reservoir of FIG. 29; and FIG. 32 is an enlarged partial section view fragment of the lid and fragrance reservoir of FIG. 31 with the lid closed and closing off or substantially sealing the container.

DETAILED DESCRIPTION OF THE PREFERRED EMBODIMENT

Figure 2A:
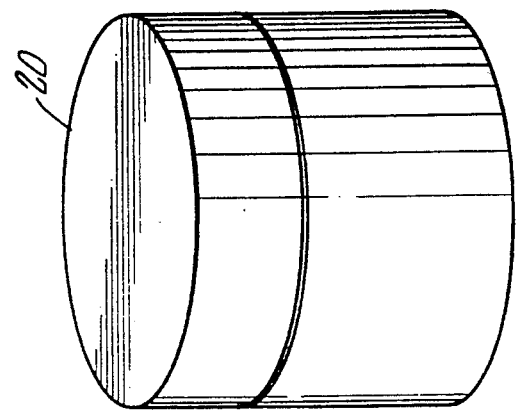
FIG. 2a is a perspective view of a second preferred embodiment of a fragrance-emitting container.

The container designs and methods herein provide a consumer with exposure to desirable fragrances associated with skin care products without risking the change of fragrance-induced skin irritation. Rather than introducing fragrance-producing chemicals into the product formulation which is applied to the skin, fragrance chemicals are incorporated into the container from which it is released when the container is touched, manipulated or opened. The fragrance reservoir may be located either in the body of the container which contains the skin care product, or alternatively, in the lid of the container. In fragrance-emitting containers having subassemblies in addition to the lid and container body (e.g., the aerosol pump mechanism displayed in FIGS. 5a–5d, 6 and 7), the fragrance reservoir may also be located therein. Under certain circumstances, it may be desirable to locate fragrance chemicals in multiple portions of the container assembly, e.g., in both the container body and in the lid, and/or in additional subassemblies which may be present.

It is intended that the present invention not be restricted in application to any particular design of container or product. The present invention may be applied to any container design which is used to hold and dispense products for skin care or other use. Such contained products may hereinafter be referred to as "product formulations". Examples of skin care products include, but are not limited to: skin creams; ointments; salves; gels; pastes; foams; balms; liquids; lotions; suspensions, emulsions and complexes; oils; serums; sprays and mists; moisturizers; toners, conditioners and fresheners; astringents; masques, muds and packs; powders; foundations, blushes, finishes and makeups; lipsticks and lip-coloring products; lip balms; eyelash treatments and conditioners; eye shadows; nail polishes, conditioners and treatments; hair care products, shampoos, conditioners, styling and coloring products; shaving creams, gels or other shaving products; skin cleansers, soaps, detergents, scrubs, and makeup removers; pads, sponges or brushes used for scrubbing, cleansing or skin care; deodorants and antiperspirants; tooth pastes, gels, liquids and tooth care products; skin tanning accelerators and products; sunscreens and environmental protectors and treatments; which may be used in cosmetics, skin hygiene, skin protection or therapeutic applications.

It is further within the scope of the present invention to use fragrance-emitting containers for applications outside of skin care products since any application in which containers are used to contain product formulations may benefit from the addition of fragrance-emitting container design. The invention is particularly useful in cases where it is specifically desired to provide a source of fragrance but where it is desired to avoid contamination of any contained product formulation with fragrance chemicals because, for example, such formulation is to be applied to or within the body, ingested or otherwise used without the presence of contaminating fragrance chemicals. Such applications include, but are not limited to containers for food products, vitamins or substances ingested for expected health benefits, containers for tablets or capsules used in therapeutic medications or any products which are intended to be ingested by humans or animals. Additionally, fragrance-emitting containers may be used to emit fragrances which act to mask or otherwise disguise contained substances which have unpleasant odors (e.g., fluids or secretions or specimens collected from humans or animals during medical procedures, medical specimens, cleaning fluids or solvents, fertilizers, human or industrial wastes). In the broadest sense, it is intended that fragrance-emitting containers be used in any applications where it is not desirable or practical or convenient to incorporate fragrance-producing chemicals into the formulation of the product itself.

Referring now in detail to the drawings, FIGS. 1a–c illustrate a fragrance-emitting container 20 having a lid assembly 22 and a body assembly 24. The body assembly 24 has a container body 26 having a fragrance reservoir well 28 and a neck 30. Preferably the neck 30 has screw threads 32. A fragrance reservoir 34 is secured within the fragrance reservoir well 28 by anchor ports 36. The lid assembly 22 has a lid 46 including a land 44 and a rim 42. A lid ring seal 38 is dimensioned to sit on the land 44. A lid plate seal 40 is disposed within the lid 46. Lid threads 48 are threadably engageable to the threads 32 on the neck 30 of the container body 26. The container body 26 has an opening 54 to access the contents of the container within the container chamber 62. FIG. 2 shows an alternative preferred embodiment wherein the fragrance reservoir well and fragrance reservoir are in the lid rather than the container body. FIGS. 5a–d and 6–9 illustrate a fragrance emitting spray container, in this case an aerosol spray or squirt container having a pump 50 and an intake tube 52 extending into the container body 26. Alternate spray means, such as those adapted for dispensing a pressurized liquid, a gel, a mousse, or other product formulation, may also be readily utilized. FIGS. 10a–10c, 11 and 12 illustrate a fragrance-emitting lipstick container having a lipstick 60 extending from the container body 26.

The container body 26 may be of any useful shape and size so long as it has a chamber 62 into which the product formulation is placed and an opening 54 through which the user can gain access to the product formulation. The container body 26 may be constructed of any suitable material such as those commonly used for skin care products today including plastic or other polymer, glass, metal, ceramic, wood or other solid material. The container body 26 may be manufactured by any suitable method used by those skilled in the art of container manufacturing. These methods include, but are not limited to injection molding, casting, or lathe cutting.

The FIGS. 1–4 illustrate three generic container body designs which may be used to contain products formulated as semisolids, liquids and solids.

The portion of the container to which the lid assembly 22 is attached (the container neck 30) may have spiral threads 32 onto which the lid assembly 22 is screwed. Alternatively it may lack threads in which case the lid assembly 22 may be fastened by friction and/or elastic forces exerted between the lid assembly 22 and neck 30. Any other suitable method of attaching a lid assembly to a container may be used so long as the attachment is secure and seals in the product formulation and the fragrance.

An element of this design is a space, chamber or other area into which or onto which the fragrance reservoir 34 is placed. The reservoir chamber is designated as the fragrance reservoir well 28 which, in the particular designs illustrated, is a channel or groove circumferentially located around the neck 30 of the container body 26. By contrast, in the design of a container designed to produce an aerosol or other spray (FIGS. 5 to 9), the fragrance reservoir well may be located in the aerosol spray pump mechanism 50 which, in turn, is attached to the neck 30 of the container body 26. The fragrance reservoir well in any case need not be a separately indented volume or space, such as a channel or groove, but may also be a surface or solid volume so long as it is adapted to receive and release fragrance chemicals according to the general design of the fragrance-emitting container. The fragrance reservoir well 28 must be large enough to accommodate the fragrance reservoir 34 which serves as the reservoir for the fragrance chemicals.

A particularly important feature of the fragrance reservoir well 28 is its location at a site far enough away from the container body opening 54 so as to substantially isolate the fragrance reservoir 34, and fragrance chemicals to be incorporated therein, from any contained product formulation, thereby to minimize the chance that the skin care product formulation or other product formulation could become contaminated by contact with the fragrance reservoir 34 and its fragrance chemicals. Alternatively, the fragrance reservoir well 28 can be located in close proximity to the container body opening 54 if the fragrance reservoir 34, and particularly the fragrance chemicals contained therein, are substantially isolated by physical or other means from the interior of the container body, and thus form any product formulation contained therein, in a manner which prevents any substantial contamination of product formulation by fragrance chemicals in the fragrance reservoir. In this regard, it will be seen that a structural isolating means such as neck 30 may be employed. Other such means to achieve substantial isolation, such as appropriate distance separation between the fragrance reservoir 34 and the interior of the container body and/or its contained product formulation, may also be used and will take into account the migration characteristics of the fragrance chemicals from the fragrance reservoir and the receptivity of the product formulation to fragrance chemical molecules. Substantial isolation signifies a degree of prevention of contamination, with respect to the particular product formulation and fragrance chemicals used, such that the user or consumer does not perceive the presence of an undesirably high level of fragrance chemical contamination of the product formulation. Optimally, this isolation will be such that very little fragrance, and most preferably no fragrance, will be detectable by smell in the product formulation itself even after extended periods (e.g., years) of product formulation storage in the container, and consumers using the product formulation do not experience adverse reactions (e.g., skin irritation) due to presence of contaminating fragrance chemicals. Also optimally, such isolation should be achievable even under circumstances where the container has not been completely or securely closed or fastened by the consumer, e.g., where the lid has been loosely screwed.

Figure 2B:
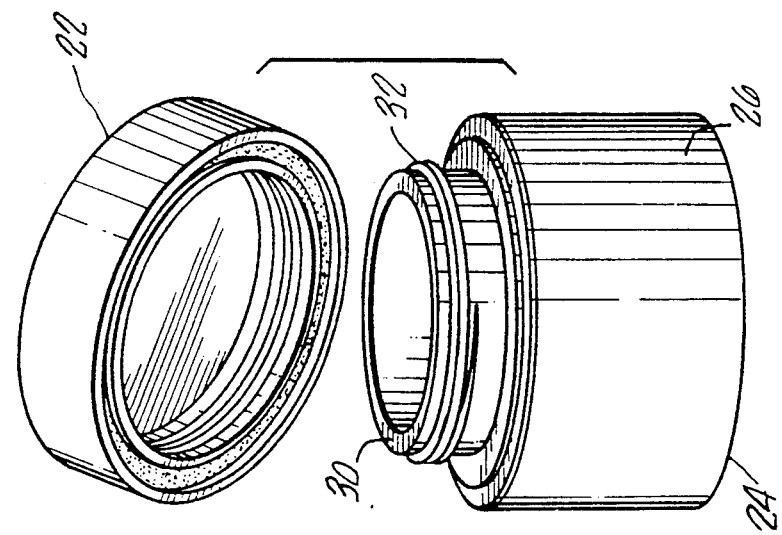
FIG. 2b is a perspective view of the container FIG. 2a with the lid removed.
Figure 2C:
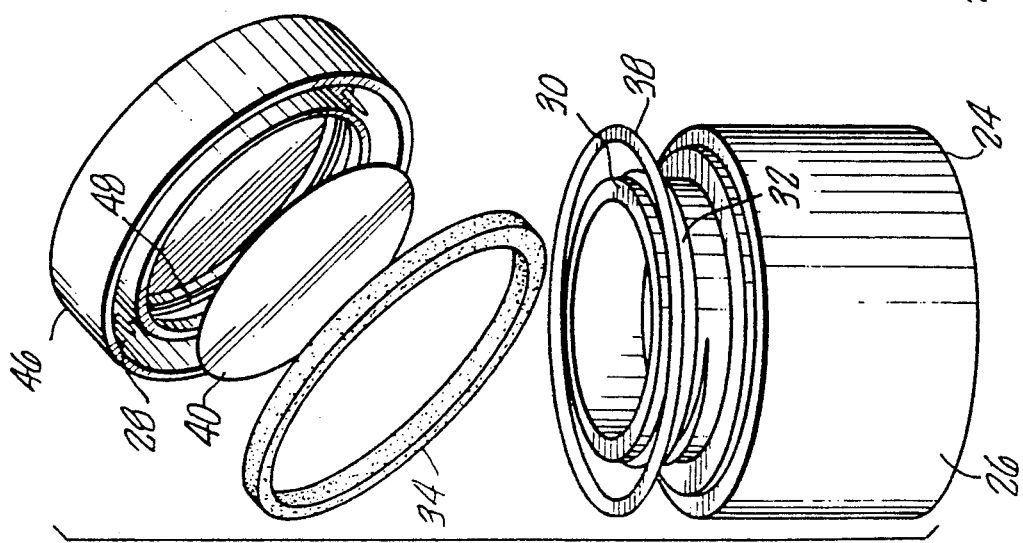
Figure 3:
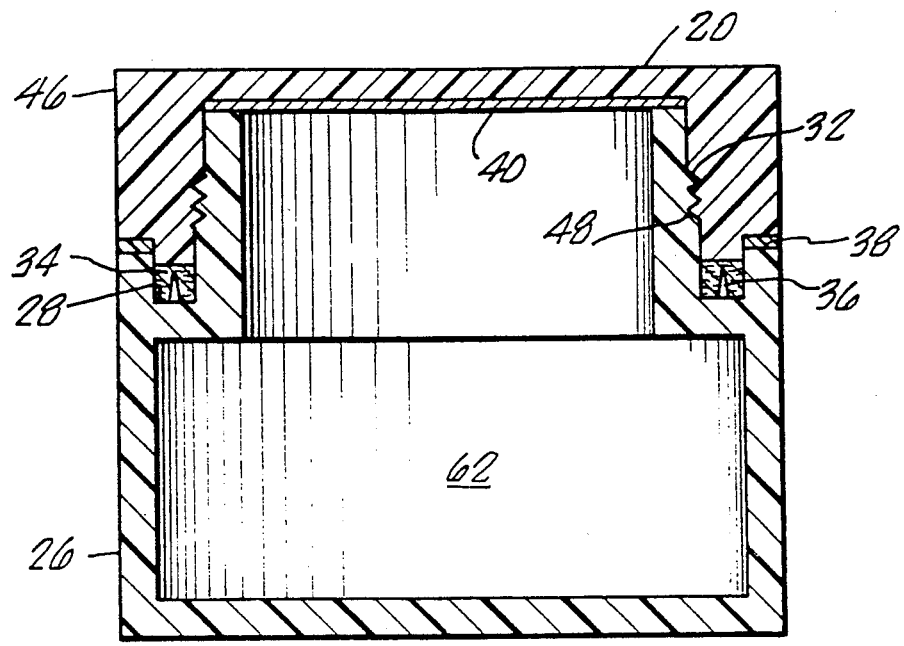
Figure 4:
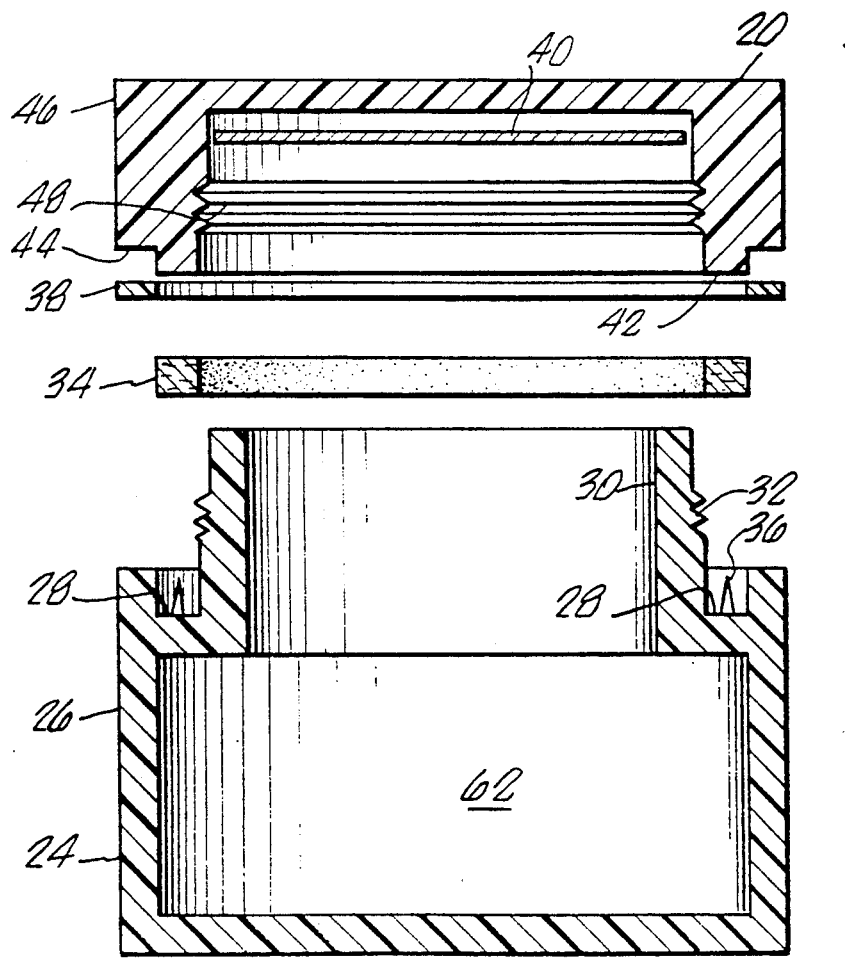
Figure 5A:
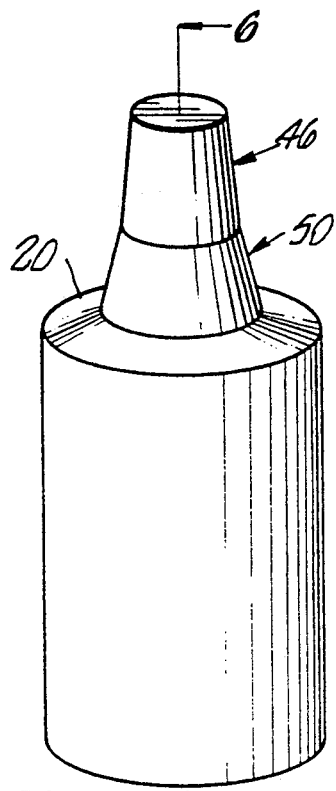
FIG. 5a is a perspective view of a fragrance-emitting aerosol container.
Figure 5B:
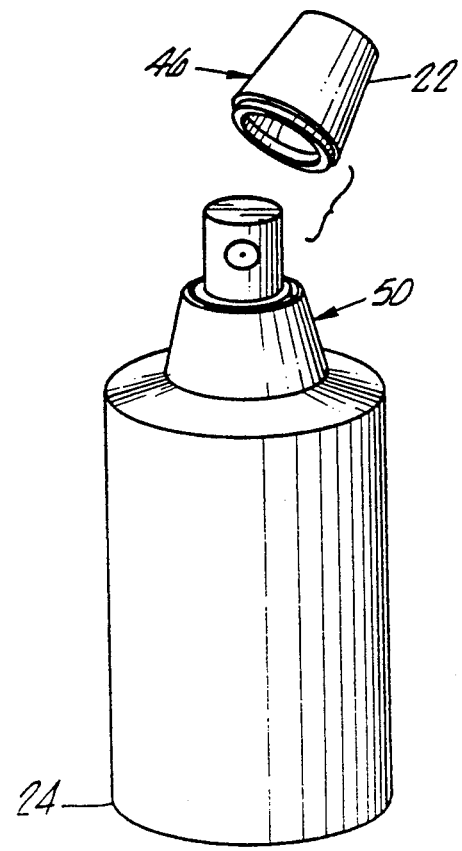
FIG. 5b is a perspective view thereof with the lid removed.
Figure 5C:
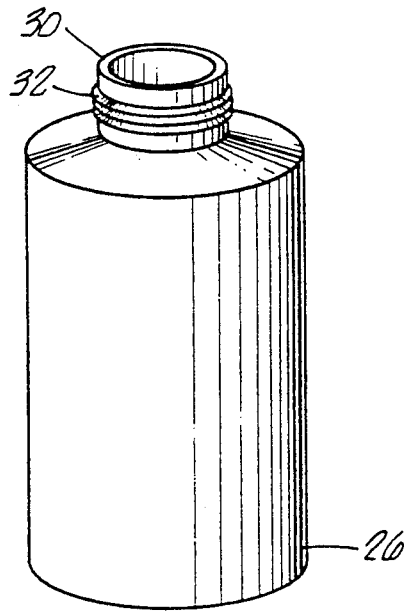
Figure 5D:
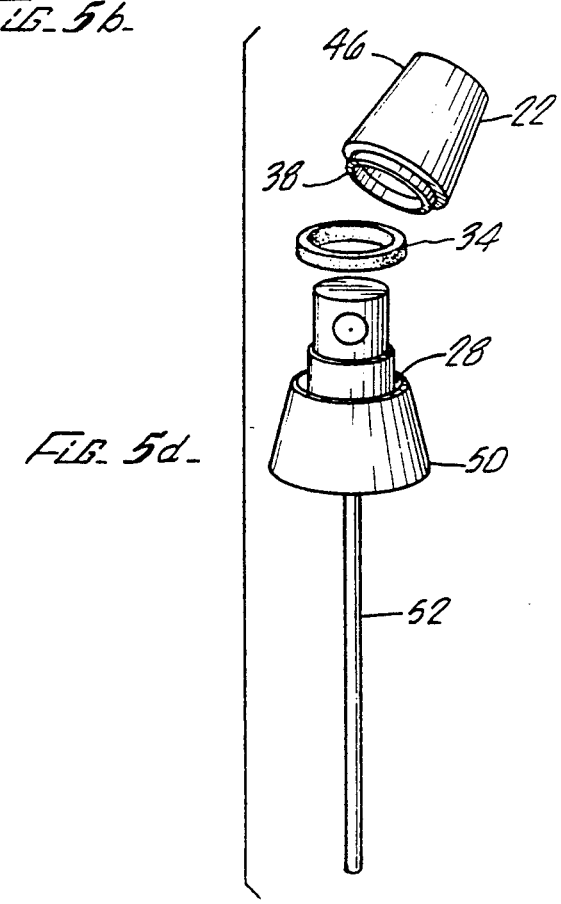
Figure 12:
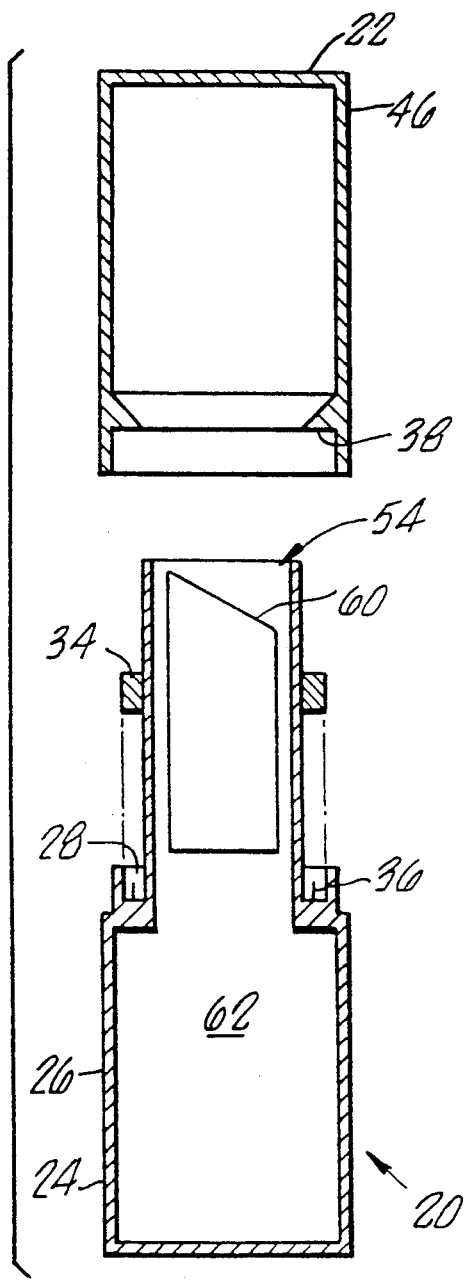
FIG. 12 is an exploded section view thereof.

In an alternative embodiment displayed in FIGS. 2a-c, the fragrance reservoir well 28 may be located in the lid assembly 22 instead of the container body 26. Any location within the lid assembly 22 may be employed so long as the fragrance reservoir well 28 is constructed to prevent the contamination of the product formulation by contact with the fragrance reservoir 34. Alternatively, the fragrance reservoir 34 may be located in both the container body 26 and in the lid assembly if, for example, it is intended that two or more distinct fragrances are to be released.

The fragrance reservoir well 28 may have as a component of its design one or more anchor pins, shafts or posts which protrude from the bottom or sides of the well. These serve to anchor the fragrance reservoir 34 to the floor of the well 28 by puncturing or otherwise contacting the fragrance reservoir upon its placement into the well. The anchor posts 3 tend to immobilize the fragrance reservoir by the friction produced between them and the reservoir material. These anchor posts may be of any shape which facilitate their ability to puncture and/or otherwise secure the fragrance reservoir without breaking it. Particularly preferred shapes will be thin, blunt, tapered or pointed at the end which contacts the fragrance reservoir. Anchor posts may be constructed out of the same material as the fragrance reservoir well, or alteratively, may be constructed out of any other suitable material such as metal, plastic or other polymer, glass, ceramic or other solid material.

Figure 13:
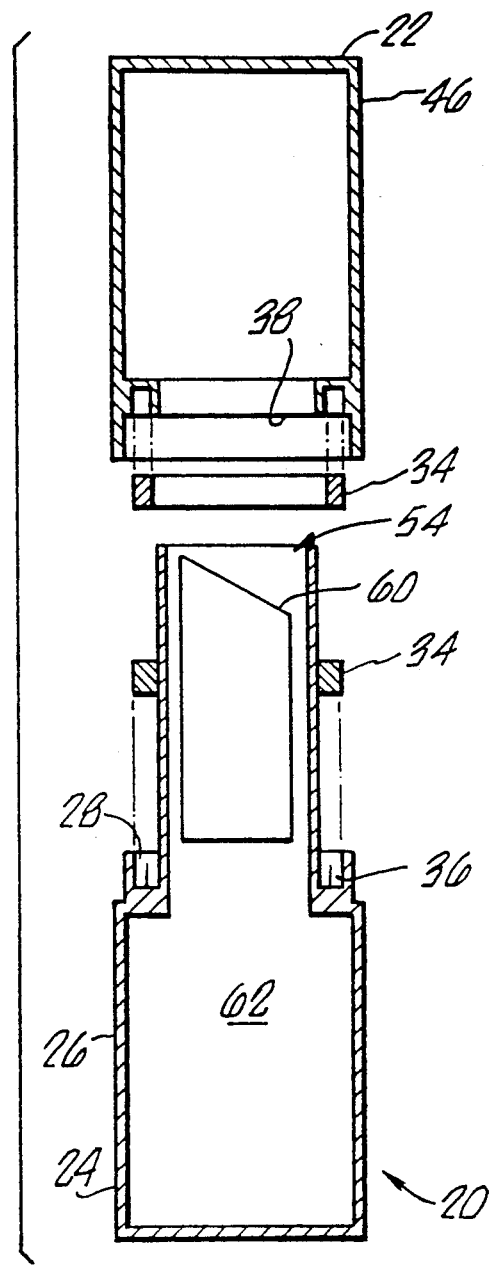
FIG. 13 is a partial section view showing an embodiment having two fragrance reservoirs.

An alternative method of securing the fragrance reservoir to the fragrance reservoir well is through the use of one or more "lips" or flanges of material which protrude into the well from its side wall(s) which act to secure the fragrance reservoir into the well. Such fragrance reservoir retaining lips 58 (as shown in FIGS. 1b and 1c) may be either continuous extensions of the inner and/or outer wall of the fragrance reservoir or, alternatively, may be discrete segments of material which protrude from the inner and/or outer wall into the reservoir well. Depending on the particular design, retention may be achieved by one or more insertable retaining elements, such as barriers, tabs, wedges, lip or flange elements 56 (as shown in FIG. 13), screws or rivets, covers, or the like, which may, for example, snap into the reservoir well over the fragrance reservoir, and which secure and protect the fragrance reservoir but which have openings, intervening spaces or other means which allow the escape of the fragrance from the container. Retention may also be achieved by friction, flexure or other forces between the fragrance reservoir and the fragrance reservoir well, or by deformation of the well or reservoir after insertion of the fragrance reservoir (as for example by heat deformation). Other methods commonly used to secure two objects together, for example adhesives or thermal welding, may be also used either alone or in combination with physical barriers to retain the fragrance reservoir in its well.

The fragrance reservoir 34 serves as the reservoir for the fragrance-producing chemicals. The fragrance reservoir may be a discrete substrate constructed of any material into which the fragrance chemicals can be incorporated (e.g., adsorbed, absorbed, coated, dissolved, adhered, etc.) or otherwise received without being substantially chemically altered, and from which the fragrance chemicals can be suitably released. An optimum feature of such a material is porosity to the fragrance chemicals which serves to increase the surface area to which the fragrance chemicals can adhere. The material should also be chemically non-reactive with the fragrance chemicals to maximize their stability during storage and use. An optimal material will be able to store and release the fragrance chemicals for the intended shelf and useful life of the skin care product, optimally several years or more.

The reservoir may also be formed from a liquid, viscous gel, paste, solid or encapsulated form of the fragrance-producing chemicals themselves which would not use a second discrete physical structural material or substrate to act as a physical reservoir for the chemicals. The gel, paste, solid, etc. can be placed into the reservoir well and act as the fragrance reservoir. Alternatively, the fragrance chemicals may be physically mixed or chemically combined with the material used to produce all or a portion of the container lid, body or other container components so long as the resultant fragrance reservoir substrate material releases the fragrance when the container is touched, manipulated or opened and does not contaminate the product formulation.

Especially preferred materials for the fragrance reservoir in the form of a discrete substrate or other solid volume are porous, flexible or elastomeric polymers which are non-reactive with the fragrance-producing chemicals and which retain and release the fragrance chemicals into the air for an extended period of time. Specific chemical compositions which are particularly preferred include ultra-high molecular weight polyethylene, high-density polyethylene, low-density polyethylene, very low-density polyethylene and other forms of polyethylene.

Alternate materials which may be used to construct a fragrance reservoir substrate include, but are not limited to: polypropylene, polytetrafluoroethylene, polyvinylidene fluoride, ethylene-vinyl acetate, ethylene-vinyl alcohol, polystyrene styrene-acrylonitrile, polyamides (e.g. nylon 6), polysulfone, polyarylate, polycarbonate, polyester, polyphthalate carbonate, polyetherimide, styrene-butadiene co-polymer, polyphenylene oxide, polyurethane foam or other foams, sintered glass or metal, porous ceramics or clay, cloth—especially felts having either natural or synthetic fibers, cardboard, pasteboard, compressed paper or woodpulp, wood or other plant-derived material or other suitable material having the specified physical characteristics.

The materials used to construct the fragrance reservoir may not be chemically pure, but may instead be combined with other chemicals or substances, including various combinations or mixtures of the above-mentioned materials or their equivalent, which may provide particularly preferred physical, chemical or aesthetic characteristics such as elasticity, the ability to optimally store and release fragrance chemicals or color.

It is intended that the fragrance reservoir may be introduced into the fragrance ring well or other fragrance well either during the container's manufacturing process, during the process of filling the container body with product formulation, or alternatively, by the consumer at the time of first or subsequent use. Likewise, it is intended that one or more fragrance chemicals may be introduced into the fragrance reservoir either during container or reservoir manufacturing, container filling or by the customer upon use. The various components of the container, including particularly the fragrance reservoir and/or its included fragrance chemicals may, of course, be manufactured separately and packaged for storage and later combination with the other components of the container if desired. It is intended that for any single product container, there may be available several different fragrance reservoirs available, each of which may contain a different fragrance. Alternatively, fragrance reservoirs which contain different intensities of fragrances may be offered to consumers. Such flexibility will allow the consumer to select the fragrance and intensity of his or her preference for use with a particular product. It will be appreciated that the present invention embraces containers within the scope of the disclosure whether filled or yet unfilled with product formulation, and whether incorporating or not yet incorporating the desired fragrance chemicals and/or fragrance reservoir.

In an alternate embodiment, the fragrance reservoir may not be a ring shape, but instead may be any suitable shape which can be incorporated into the container body, lid, or container subassembly. It is particularly intended that the present invention not be limited to any particular form or shape of the fragrance reservoir. The reservoir material may be deformable so as to be shaped as desired, as for example a deformable strip which may be bent into a ring or other shape.

The chemicals or substances which are used to produce a desired fragrance may be any one or more of which are commonly used by those skilled in the art of fragrance chemistry or perfumery, some of which are listed in the following texts: Rüdiger Hall, Dieter Klemme, Jürgen Nienhaus, *Guide To Fragrance Ingredients*, H&R Edition, R. Glöss & Co. Publishing, Hamburg, 1985; Julia Müller, *The H&R Book of Perfume*, H&R Edition, Johnson Publications Ltd., London, 1984; *Fragrance Guide-Feminine Notes, Masculine Notes*, H&R Edition, R. Glöss & Co. Publishing, Hamburg, 1985 which are incorporated by reference herein.

It is specifically intended that the present invention not be limited to any particular fragrance or combination of fragrances, whether known or discovered in the future since any fragrance or chemical substances which humans find pleasant and desirable to inhale are within the scope of the present invention.

It is also intended that for certain applications, chemicals which do not produce a detectable scent but instead produce certain biological or psychological effects may be incorporated into the fragrance reservoir alone or in combination with fragrance-producing chemicals. These substances include, but are not limited to pheromones which may alter the sexual behavior of humans, hormones which may alter the physiology of the body, mood-altering substances, organ extracts, plant extracts or other materials or chemicals which provide a desired biological or psychological effect. The use of the term "fragrance" or "fragrance chemicals" herein includes these substances as well.

The fragrance chemicals may have a variety of physical forms which include, but are not limited to: liquid, gel, cream or other semisolid, solid, powder or gas. Additionally, the fragrance chemicals may be encapsulated into small or microscopic "beads" or enclosures using any technique commonly used for chemical encapsulation. It will be recognized that fragrance chemicals may be mixed or combined with various solvents, diluents or other substances which act to dissolve the fragrance chemicals or alter their intensity, stability, viscosity, rate of release or other physical or chemical characteristics.

The lid ring seal 38 displayed in the figures is attached to or part of the lid assembly 22 and or the container body 24 and serves to seal in the fragrance while the lid is on the container. The lid seal may be an integral part of the lid assembly 22 or container body design or alternatively may be a separate structure which is attached to the lid 46 or container body 24. In the design displayed in FIGS. 2a-2c where the fragrance reservoir is attached to the lid, the lid seal is located on the body or neck of the container and may be similarly integral to the container body or a separate structure which is attached to the container body.

An important attribute of a lid and/or lid seal may be their ability to effectively cover or otherwise obstruct the fragrance reservoir when the container is closed, as for example by physically covering the opening of the fragrance reservoir well to the outside. A lid or lid seal will be deemed adequate for this purpose when it substantially prevents the release of the fragrance when the lid is fastened or otherwise attached to the container body but readily allows fragrance to be released when the lid is manipulated, opened, removed or otherwise released from the container body, depending on the particular design of the container. The releasable attachment of the lid to the container body may be accomplished by complete removal of the lid, as by the unscrewing of a discrete lid element, by partial removal, as by twisting or snapping of the lid to an open position while still being connected to the container body, or by other manipulation. The substantial prevention of such release may be verified by smell, as for example by a low or non-existent level of fragrance release after the container is closed, or by objective use criteria such as the ability of the closed container to retain a sufficient reservoir of fragrance chemicals over the intended life of the container device. Optimally, such substantial prevention or release should be achievable even under circumstances where the container has not been completely or securely closed or fastened.

The lid 46 may be constructed of any suitable material which is non-reactive with the skin care product and which adequately seals the container and prevents leakage. The lid may be fastened to the container body by either standard spiral threads or be fastened by the effect of friction between the lid and its point of contact with the container. It is understood that the present invention does not seek to limit the design of the lid to any particular form or fastening method since any suitable design having the stated properties will suffice.

The lid may be manufactured by any suitable method used by those skilled in the art of container manufacturing. These methods include, but are not limited to injection molding, casting, or lathe cutting.

For many applications, consumers desire to enjoy the scent of pleasant fragrances. One embodiment of the present invention provides for container designs which release pleasant fragrances when the container lid is opened. In one intended use of a fragrance-emitting container, the fragrance released will produce a soothing, calming and potentially therapeutic effect on the person who opens the container. Certain fragrances such as lavender, among others, have been reported to produce a calming effect on people, for example.

Among the many circumstances in which a soothing fragrance-emitting container will be useful, particularly useful settings include hospitals and clinics, schools and work environments. Containers used to hold products used by or around babies will also be particularly useful to calm the baby and potentially to reduce the tendency to cry.

For other applications, it may be desirable to produce stimulation or alertness. For these goals, different fragrances may be used.

Examples of specific containers contemplated include cosmetic organizer boxes used to hold cosmetics and products and accessories used for skin and hair care, jewelry containers, containers or holders for photographs, containers used to hold school or work-related items such as pencil or pen boxes, containers used to hold products used by or around babies and containers for pocket mirrors.

One important aspect of the present invention is that the fragrance chemicals do not contact the container contents and thus cannot produce irritation or other untoward effects on the user. For example upon opening a cosmetic organizer case, the user will experience a pleasant scent emitting from the case but will not risk skin irritation from the use of the products stored within the case. Similarly, the jewelry stored with a fragrance-emitting jewelry case will not be contaminated with potentially irritating fragrance chemicals. A photograph container or a container used to hold "keepsakes" having sentimental value, when opened, may release the fragrance associated with a loved one without potentially damaging the photographs or keepsakes by contact with the fragrance chemicals.

As shown in FIG. 14, a cosmetic organizer 70 or other container includes a container body 72 having a front panel 74, a back panel 76, opposite side panels 78 and a bottom 80. A container cover 82 is preferably pivotally attached to the back panel 76. Alternatively, the cover 82 may also be a separate piece which may be fitted over the container body 72. As shown in FIGS. 14, 15 and 18, the front panel 74 has a channel or recess 84 holding a first fragrance reservoir 86. The fragrance reservoir 86 is of the same design as the fragrance reservoirs previously described.

As shown in FIGS. 16 and 17, a center partition 88 extends across the container body 72 forming an interior compartment 90. A compartment cover 92, preferably pivotally attached to the left side wall 78 covers the interior compartment 90. Lateral partitions 94 may also be provided to divide the container body into additional and smaller compartments 96. A center partition channel or recess 98 contains a second fragrance reservoir 100, as shown in FIGS. 16 and 19.

Referring to FIGS. 18, 19 and 20, with the container cover 82 in the down or closed position, the first fragrance reservoir 86 is covered over and sealed by the container cover 82. Hence, little or no fragrance can flow from the first fragrance reservoir 86 into the interior of the container body 72, or outside to the environment. Similarly, with the compartment cover 92 closed, as shown in FIG. 20, the second fragrance reservoir 100 is also closed or sealed, to substantially prevent fragrance from escaping into the first interior compartment 90, or into the container body 72, or into the environment.

As shown in FIGS. 14-18 with the container cover 82 partially or fully opened, the first fragrance reservoir 86 is unsealed and opened to the container body and the environment. Accordingly, lifting the container cover 82 releases fragrance from the first fragrance reservoir 86, providing the potentially enjoyable scent of pleasant fragrances to the user, as well as potential soothing, calming or therapeutic effects.

With the container cover 82 fully opened, the compartment cover 92 can then also be opened, releasing fragrance from the second fragrance reservoir 100. The fragrances from the first and second reservoirs preferably have complimentary results with each other when mixed, i.e., when the container cover 82 and compartment cover 92 are both opened. The remaining lateral compartments 96 within the container body 72 may remain closed with their own covers, to prevent fragrance from the first and second reservoirs from contacting the contents of the lateral compartments 96. Alternatively, the lateral compartments, or other compartments within the container body, may have their own compartment covers and channels or recesses containing additional fragrance reservoirs.

In many instances, containers are used to hold objects or substances which emit unpleasant odors. These odors may derive from human or animal wastes, excrement, tissues, fluids or gasses; garbage, trash or food waste; products of decay or decomposition, cleaning products or solvents, substances used in manufacturing processes, products of combustion or other objects or substances. More specific examples of contained items and containers which are contemplated in the present invention include wastes from medical procedures, soiled diaper containers, dirty laundry hampers, containers for shoes or athletic gear, cat litter boxes, garbage or trash, laundry detergents or similar cleaning products, fishing tackle boxes and ash trays.

In all cases in which the odor released is objectionable, it is desirable to "mask" or otherwise disguise the objectionable odor with a pleasant or neutral fragrance when the container is opened. During the time that the container is closed, the fragrance reservoir is also closed since the container's objectionable odors are confined to the interior of the container and are thus not readily detectable. By contrast, when the container is opened, either partly or completely, the objectionable odor can escape into the surroundings and the masking fragrance is simultaneously released to disguise and camouflage the objectionable odor.

As shown in FIGS. 22-26, a container 110 for holding, e.g., dirty laundry, trash, waste products, cigarette ashes, etc., includes a cover 112 preferably pivotally attached to the container 110. A front wall 114 of the container 110 has a channel or recess 116 holding a fragrance reservoir 118. With the cover 112 closed, as shown in FIGS. 21 and 26, the fragrance reservoir 118 is substantially sealed from the interior of the container and from the environment. The degree of sealing provided may vary with the application, from the seal provided simply by the cover resting over the front wall, to a more substantial seal using rubber surfaces, etc. With the cover 112 open, as shown in FIGS. 23-25, the fragrance reservoir 118 is unsealed and fragrance escapes from the reservoir 118 to mask or neutralize unpleasant odors emanating from the contents of the container 110.

As shown in FIGS. 27-32, the fragrance reservoir may optionally be provided in a recess or channel in the container lid. The fragrance reservoir may be secured in the lid (or to the container body itself) using the posts and other retaining means previously shown and described. Similarly, the container 110 may include fragrance reservoir in both the lid and container body.

Thus, although several embodiments have been shown and described, it will be apparent to those skilled in the art that many modifications can be made without departing from the spirit and scope of the invention. It will also be apparent that the various features of the various embodiments may be used separately or in combination with each other. The invention, therefore, should not be restricted except by the following claims.

I claim:

1. A fragrance emitting container comprising:
   a container body substantially enclosing a container space;
   a channel in the container body;
   a fragrance reservoir containing a fragrance positioned in the channel; and
   a container lid pivotably attached to the container body, the container lid movable from a closed position wherein the container lid covers the container space and at least partially seals the fragrance reservoir, to an open position wherein the container space and fragrance reservoir are uncovered such that fragrance can disperse from the channel.

2. The fragrance emitting container of claim 1 further comprising a seal on at least one of the container lid and container body for sealing the channel when the lid is in the closed position.

3. The fragrance emitting container of claim 1 further comprising:
   a subcontainer within the container body substantially enclosing a subcontainer space;
   a subcontainer fragrance reservoir supported on the subcontainer; and
   a subcontainer lid pivotably attached to the container body, the subcontainer lid movable from a closed position wherein the subcontainer lid covers and at least partially seals off the subcontainer space and the subcontainer fragrance reservoir, to an open position wherein the subcontainer space and subcontainer fragrance reservoir are uncovered.

4. A fragrance emitting container comprising:
   a container body substantially enclosing a container space;
   a container lid pivotably attached to the container body;
   a fragrance reservoir containing a fragrance positioned in a recess in the container lid, the container lid movable from a closed position wherein the recess is at least partially sealed off, to an open position wherein recess is open such that fragrance can disperse from the channel.

5. A fragrance emitting container comprising:
   a container body substantially enclosing a container space;
   a channel in the container body;
   a fragrance reservoir containing a fragrance in the channel; and
   a container lid removably positionable onto the container body, the container lid covering and at least partially sealing the channel when positioned on the container body, and the channel open to the container space when the container lid is removed from the container body, thereby allowing the fragrance to disperse.

6. The fragrance emitting container of claim 5 further comprising:
   a subcontainer within the container body substantially enclosing a subcontainer space;
   a subcontainer fragrance reservoir supported on the subcontainer; and
   a subcontainer lid removably positionable onto the subcontainer body, the subcontainer lid movable from a closed position wherein the subcontainer lid covers and at least partially seals off the subcontainer space and the subcontainer fragrance reservoir, to an open position wherein the subcontainer space and subcontainer fragrance reservoir are uncovered.

7. A fragrance emitting container comprising:

a container body substantially enclosing a container space;

a container lid engageable onto to the container body;

a fragrance reservoir containing a fragrance, and forming a section of at least one of the body and lid at a location such that the fragrance reservoir is at least partially sealed off from the container space when the lid is engaged onto the body and the reservoir is open to the container space when the lid is not engaged to the container body.

* * * * *